United States Patent
Zhao et al.

(10) Patent No.: US 11,664,116 B2
(45) Date of Patent: May 30, 2023

(54) MEDICAL IMAGE DATA

(71) Applicant: Siemens Healthcare GmbH, Erlangen (DE)

(72) Inventors: Yu Zhao, Athens, GA (US); Parmeet Bhatia, Paoli, PA (US); Ke Zeng, Bryn Mawr, PA (US); Gerardo Hermosillo Valadez, West Chester, PA (US); Chen Li, West Lebanon, NH (US); Zhigang Peng, Ambler, PA (US); Yiyuan Zhao, Malvern, PA (US)

(73) Assignee: Siemens Healthcare GmbH, Erlangen (DE)

( * ) Notice: Subject to any disclaimer, the term of this patent is extended or adjusted under 35 U.S.C. 154(b) by 175 days.

(21) Appl. No.: 17/109,505

(22) Filed: Dec. 2, 2020

(65) Prior Publication Data

US 2021/0249119 A1 Aug. 12, 2021

(30) Foreign Application Priority Data

Feb. 7, 2020 (EP) .................................... 20156247

(51) Int. Cl.
*G16H 30/40* (2018.01)
*G06T 7/62* (2017.01)
(Continued)

(52) U.S. Cl.
CPC ........... *G16H 30/40* (2018.01); *G06T 7/0012* (2013.01); *G06T 7/11* (2017.01); *G06T 7/62* (2017.01);
(Continued)

(58) Field of Classification Search
CPC .. G16H 30/40; G06T 7/62; G06T 7/11; G06T 7/0012; G06T 2207/10081;
(Continued)

(56) References Cited

U.S. PATENT DOCUMENTS

2008/0273775 A1* 11/2008 Hilbelink .............. G06T 7/0012
382/128
2015/0173715 A1* 6/2015 Raghavan .............. G16H 40/67
600/443
(Continued)

FOREIGN PATENT DOCUMENTS

EP 3355273 A1 8/2018

OTHER PUBLICATIONS

Manko. "Segmentation of Organs at Risk in Chest Cavity Using 3D Deep Neural Network" 2019 Signal Processing Symposium (SPSymp), 2019. (Year: 2019).*
(Continued)

*Primary Examiner* — Vu Le
*Assistant Examiner* — Julius Chai

(57) ABSTRACT

Disclosed is a method, a computer readable storage medium and an apparatus for processing medical image data. Input medical image data is received at a data processing system, which is an artificial intelligence-based system. An identification process is performed at the data processing system on the input medical image data to identify a volume of interest within which an instance of a predetermined anatomical structure is located. First and second determination processes are performed at the data processing system to determine, respectively, first and second anatomical directions for the instance of the anatomical structure that are defined relative to the coordinate system of the input medical image data. Output data relating to the first and second anatomical directions is output from the data processing system.

18 Claims, 8 Drawing Sheets

(51) Int. Cl.
*G06T 7/11* (2017.01)
*G06T 7/00* (2017.01)

(52) U.S. Cl.
CPC ............... *G06T 2207/10081* (2013.01); *G06T 2207/10088* (2013.01); *G06T 2207/20081* (2013.01); *G06T 2207/20084* (2013.01); *G06T 2207/30012* (2013.01)

(58) Field of Classification Search
CPC . G06T 2207/10088; G06T 2207/20081; G06T 2207/20084; G06T 2207/30012
See application file for complete search history.

(56) References Cited

U.S. PATENT DOCUMENTS

2016/0260213 A1* 9/2016 Reda .................. G06T 19/20
2018/0218516 A1* 8/2018 Reda .................. G06T 7/11
2020/0170807 A1* 6/2020 Bettenga ................ A61B 5/064
2022/0160430 A1* 5/2022 Landon .................. G06F 30/12

OTHER PUBLICATIONS

Bhatia, Parmeet S., et al. "Real time coarse orientation detection in MR scans using multi-planar deep convolutional neural networks." Medical Imaging 2017: Image Processing. vol. 10133. International Society for Optics and Photonics, 2017.

Hesamian, Mohammad Hesam, et al. "Deep learning techniques for medical image segmentation: Achievements and challenges." Journal of digital imaging 32.4 (2019): 582-596.

Reda, Fitsum A., Yiqiang Zhan, and Xiang Sean Zhou. "A steering engine: Learning 3-d anatomy orientation using Yegression forests." International Conference on Medical Image Computing and Computer-Assisted Intervention. Springer, Cham, 2015.

Manko, M. (Sep. 2019). Segmentation of Organs at Risk in Chest Cavity Using 3D Deep Neural Network. In 2019 Signal Processing Symposium (SPSympo) (pp. 287-290). IEEE.

* cited by examiner

MEDICAL IMAGE DATA

RELATED APPLICATIONS

This application claims benefit of EP Patent Application No. 20156247.7 filed on Feb. 7, 2020, the contents of which of hereby incorporated by reference.

TECHNICAL FIELD

The present invention relates to processing medical image data. The processing involves a data processing system which is an artificial intelligence-based system.

BACKGROUND

Medical imaging techniques may be used to obtain information regarding a human or animal body. For example, X-ray images can be used to image the bones of a patient (e.g. to detect and classify bone fractures) and may also be used to image soft tissues and the circulatory system, for instance by using a contrast agent. In another example, Magnetic Resonance Imaging (MRI) can be used to image various tissues of the body, for instance to identify tumors, or to investigate possible soft-tissue injuries (e.g. tendon or muscle tears).

When imaging a specific anatomical structure within a human or animal body, such as a particular joint, there will typically be some variation in the orientation of the anatomical structure from one imaging session to another. For example, for two sessions carried out on the same patient, the patient may have been in different positions. Moreover, for two sessions carried out on different patients, there is an even greater likelihood that the two patients were in different positions for their respective imaging sessions. These factors, and others, result in there being uncertainty in the orientation of the anatomical structure, as it is represented in the dataset produced in the scanning session.

However, knowing the orientation of an anatomical structure within the dataset from a specific imaging session may be useful for various reasons. For example, it may assist in later analysis of the dataset, whether such analysis is carried out by a medical professional or by a data processing system. While possible, it is complicated and time consuming for a medical professional to determine the orientation of an anatomical structure in multiple datasets, especially in a consistent manner. Moreover, although some efforts have been made to develop data processing systems capable to determining orientation of anatomical structures, issues remain in terms of robustness, accuracy and speed.

It is an object of the present invention to address at least some of the difficulties with the procedure for analyzing medical image data.

SUMMARY

According to a first aspect of the present invention, there is provided a method for processing medical image data. The method comprises: receiving input medical image data at a data processing system, the data processing system being an artificial intelligence-based system, the data being defined with reference to a data coordinate system; performing, at the data processing system, an identification process on the input medical image data to identify a volume of interest within which an instance of a predetermined anatomical structure is located; performing, at the data processing system, a first determination process comprising processing first volume of interest data to determine a first anatomical direction for the instance of the anatomical structure, the first volume of interest data being medical image data that is representative of the volume of interest and that is derived from the input medical image data; performing, at the data processing system, a second determination process comprising processing second volume of interest data to determine a second anatomical direction for the instance of the anatomical structure, the second volume of interest data being medical image data that is representative of the volume of interest and that is derived from the input medical image data, the first and second anatomical directions being defined with reference to the data coordinate system; and outputting, from the data processing system, output data relating to the first and second anatomical directions.

By processing data associated with a volume of interest within which the anatomical structure of interest is located, the first and second determination processes may explicitly or implicitly act on data representing landmarks associated with the anatomical structure. Hence, or otherwise, methods according to the first aspect may assist in the robust and efficient determination of anatomical directions for the anatomical structure. Furthermore, utilizing respective determination processes to determine the first and second anatomical directions for the anatomical structure is considered to suitably balance robustness and efficiency of the method.

In some examples, the data coordinate system may be a rectilinear coordinate system, such as a cartesian coordinate system. Hence, or otherwise, the data coordinate system may have three orthogonal axial directions.

In some examples, the first and second anatomical directions may be orthogonal to one another and, optionally, to a third anatomical direction.

Optionally, the output data comprise data relating to and, in specific examples, defining the volume of interest. For instance, such data may define the centre of the volume of interest and/or may define the boundary or margin of the volume of interest. Such data may enable further scans to be carried out on the volume of interest, for example at a higher level of resolution.

Optionally, the first determination process comprises a first segmentation process that determines a first planar mask, and comprises determining a direction normal to the first planar mask, and designating the normal direction for the first planar mask as the first anatomical direction, and the second determination process comprises a second segmentation process that determines a second planar mask, and comprises determining a direction normal to the second planar mask, and designating the normal direction for the second planar mask as the second anatomical direction.

It is considered that use of such planar masks may assist in achieving robust, fast and accurate determination of anatomical directions. In particular, such a segmentation process is considered to assist in the accurate determination of the anatomical directions for the anatomical structure, even where the anatomical directions are at significant angular offsets from the directions of the data coordinate system.

In examples that use planar masks, the method optionally comprises determining the normal directions for the first and second planar masks using principal component analysis. As a further option, the first volume of interest data is the same as the second volume of interest data.

Particularly (but not exclusively) in examples that use planar masks, the method optionally comprises applying a rotation operation to at least one of the first volume of interest data and the second volume of interest data, yielding processed volume of interest data, wherein the data coordinate system has three axial directions, wherein the rotation operation results in the first and second anatomical directions being in a predetermined angular relationship with the axial directions of the data coordinate system, and wherein the output data comprise the processed volume of interest data. Such processed volume of interest data may provide a consistent representation of the anatomical structure of interest, which, as discussed above, may assist in later analysis of the structure.

In examples that use planar masks, the data processing system is optionally a neural network system comprising: an identification network, which has been trained using training data comprising a set of ground truth image datasets, each of which is representative of a volume encompassing an instance of the anatomical structure and comprises information relating to a volume of interest within which that instance of the anatomical structure is located; one or more determination networks, which have been trained using training data comprising a set of ground truth image datasets, each of which is representative of an instance of the anatomical structure and comprises information relating to first and second anatomical directions for the instance of the predetermined anatomical structure; and the method comprises: performing the identification process at least in part using the identification network, and performing the first and second determination processes with the one or more determination networks. In specific examples, each of the first and second determination networks is a fully convolutional neural network; for instance, each of the first and second determination networks is a U-net, or each of the first and second determination networks is a V-net.

Employing neural networks trained using appropriate sets of training data provides a robust way of processing the medical image data. Neural networks may deal with complex medical image data and/or may provide more accurate results than other prior art computational techniques for image processing.

In some examples, the first and second determination processes may run in parallel.

However in other examples the first and second determination processes may operate, at least in part, in series, so that output from the first determination process (for example, volume of interest data, or data indicating the first anatomical direction for the anatomical structure in the data coordinate system) may, for example, be used by the second determination process.

Hence, or otherwise, the method may optionally comprise applying a rotation operation to the first volume of interest data, yielding the second volume of interest data, which is used by the second determination process. The first rotation operation results in the first anatomical direction being in a predetermined angular relationship with axial directions of the data coordinate system. For example, the predetermined angular relationship might correspond to the first anatomical direction being aligned with one of the axial directions of the data coordinate system.

Such a rotation may assist the operation of the second determination process, as the second volume of interest data may be more "recognizable" since it is closer to a standardized orientation.

As a further option, the method additionally comprises applying a rotation operation to the second volume of interest data, yielding processed volume of interest data. The second rotation operation results in the anatomical directions each being in a predetermined angular relationship with the axial directions of the data coordinate system. For example, the predetermined angular relationships might correspond to each anatomical direction being aligned with a respective one of the axial directions of the data coordinate system.

Because such processed volume of interest data is defined with reference to anatomical directions, it may provide a consistent representation of the anatomical structure. This may, for example, assist in later analysis of the data, whether carried out by a medical professional (who may find a consistent representation of the specific anatomy more intelligible) or by a data processing system, such as an artificial intelligence-based system (which may give less accurate results where the anatomical structure, as represented within the image data, is not in a standardized orientation).

In examples where the second volume of interest data is provided using such a rotation operation, the data processing system is optionally a neural network system comprising: an identification network, which has been trained using training data comprising a set of ground truth image datasets, each of which is representative of a bodily region that includes an instance of the anatomical structure and comprises information relating to a volume of interest within which that instance of the anatomical structure is located; a first determination network, which has been trained using training data comprising a set of ground truth image datasets, each of which is representative of an instance of the anatomical structure and comprises information relating to a first anatomical direction for that instance of the predetermined anatomical structure; and a second determination network, which has been trained using training data comprising a set of ground truth image datasets, each of which is representative of an instance of the anatomical structure and comprises information relating to a second anatomical direction for that instance of the predetermined anatomical structure; and the method comprises: performing the identification process at least in part using the identification network, and performing the first and second determination processes with, respectively, the first and second determination networks. In particular examples, the identification network and the first and second determination networks are capsule neural networks.

Employing neural networks trained using appropriate sets of training data provides a robust way of processing the medical image data. Neural networks may deal with complex medical image data and provide more accurate results than other prior art computational techniques for image processing.

The methods defined above may optionally comprise downsampling the input medical image data to produce downsampled medical image data. In such examples, the identification process may comprise: a low-resolution identification process, which acts on the downsampled medical image data to identify an estimated volume of interest; and a high-resolution identification process, which acts on a subset of the medical image data representing the estimated volume of interest so as to identify the volume of interest. Such an identification process is considered to assist in accurately and robustly identifying a volume of interest, while being efficient in terms of time and/or storage requirements.

In examples where such an identification process is employed, the data processing system is optionally a neural network system comprising: a low-resolution identification network, which has been trained using training data comprising a set of ground truth image datasets, each of which is representative of a bodily region that includes an instance of the anatomical structure and comprises information relating to a volume of interest within which that instance of the anatomical structure is located, and a high-resolution identification network, which has been trained using training data comprising a set of ground truth image datasets, each of which is representative of a bodily region that includes an instance of the anatomical structure and comprises information relating to a volume of interest within which that instance of the anatomical structure is located; and the method comprises: performing the low-resolution identification process using the low-resolution identification network, and performing the high-resolution identification process using the high-resolution identification network.

In particular examples, the low-resolution and high-resolution differ substantially only in that a feature size of the low-resolution network is different to a feature size of the high-resolution network.

It is considered that the methods described above may be particularly suited to application where the predetermined anatomical structure comprises one or more joints. In particular the anatomical structure may be a knee joint, a shoulder joint, a hip joint, or the spine.

Additionally or alternatively, in the methods described above the first and second anatomical directions are optionally selected from the group consisting of:

a direction normal to the sagittal plane;
a direction normal to the coronal plane; and
a direction normal to the transverse plane.

As a further option, the medical image data may comprise magnetic resonance imaging data.

According to a second aspect of the present invention, there is provided a computer readable storage medium, storing: one or more neural networks trained to identify a volume of interest in which a predetermined anatomical structure is located, and to determine first and second anatomical directions for a predetermined anatomical structure, as represented within medical image data; and instructions that, when executed by the one or more processors, cause the one or more processors to: receive input medical image data at a data processing system, the data processing system being an artificial intelligence-based system, the data being defined with reference to a data coordinate system; perform, at the data processing system, an identification process on the input medical image data to identify a volume of interest within which an instance of a predetermined anatomical structure is located; perform, at the data processing system, a first determination process comprising processing first volume of interest data to determine a first anatomical direction for the instance of the anatomical structure, the first volume of interest data being medical image data that is representative of the volume of interest and that is derived from the input medical image data; perform, at the data processing system, a second determination process comprising processing second volume of interest data to determine a second anatomical direction for the instance of the anatomical structure, the second volume of interest data being medical image data that is representative of the volume of interest and that is derived from the input medical image data, the first and second anatomical directions being defined with reference to the data coordinate system; and output, from the data processing system, output data relating to the first and second anatomical directions.

Providing a computer readable storage medium allows the advantageous method according to the first aspect to be used, for example, by medical professionals. The computer readable storage medium allows access to the method according to the first aspect which has the above described advantages.

According to a third aspect of the present invention, there is provided an apparatus for processing medical image data. The apparatus comprises one or more processors; and a memory storing: one or more neural networks trained to identify a volume of interest in which a predetermined anatomical structure is located, and to determine first and second anatomical directions for a predetermined anatomical structure, as represented within medical image data; and instructions that, when executed by the one or more processors, cause the one or more processors to: receive input medical image data at a data processing system, the data processing system being an artificial intelligence-based system, the data being defined with reference to a data coordinate system; perform, at the data processing system, an identification process on the input medical image data to identify a volume of interest within which an instance of a predetermined anatomical structure is located; perform, at the data processing system, a first determination process comprising processing first volume of interest data to determine a first anatomical direction for the instance of the anatomical structure, the first volume of interest data being medical image data that is representative of the volume of interest and that is derived from the input medical image data; perform, at the data processing system, a second determination process comprising processing second volume of interest data to determine a second anatomical direction for the instance of the anatomical structure, the second volume of interest data being medical image data that is representative of the volume of interest and that is derived from the input medical image data, the first and second anatomical directions being defined with reference to the data coordinate system; and output, from the data processing system, output data relating to the first and second anatomical directions.

The third aspect advantageously provides hardware for implementing the method according to the first aspect, which has the above-described advantages.

Optionally, the apparatus according to the third aspect comprises an imaging apparatus configured to acquire the medical image data.

Incorporating the imaging apparatus advantageously provides an apparatus which can perform the additional task of acquiring the relevant medical image data. The apparatus may be provided as a single system that can acquire the relevant medical images and also process them according to the described advantageous method.

Optionally, the apparatus according to the third aspect comprises an input interface for allowing a user of the apparatus to override and/or manually correct the output of the apparatus.

The input interface advantageously allows the user to make changes to the output as required. The user can therefore modify the output if the results are judged to be inaccurate, for example.

BRIEF DESCRIPTION OF THE DRAWINGS

The present invention will now be described, by way of example only, with reference to the accompanying drawings in which.

Figure 4:
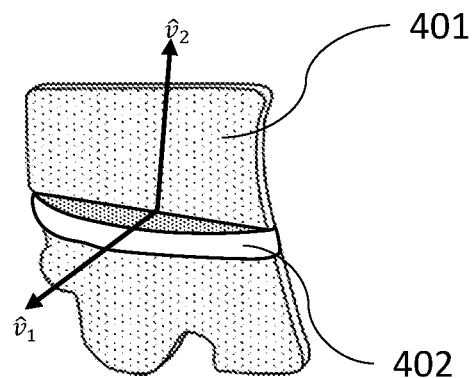
FIG. 4 illustrates processes for determining anatomical directions for an anatomical structure that may be performed as part of the method illustrated in FIG. 1.
Figure 5:
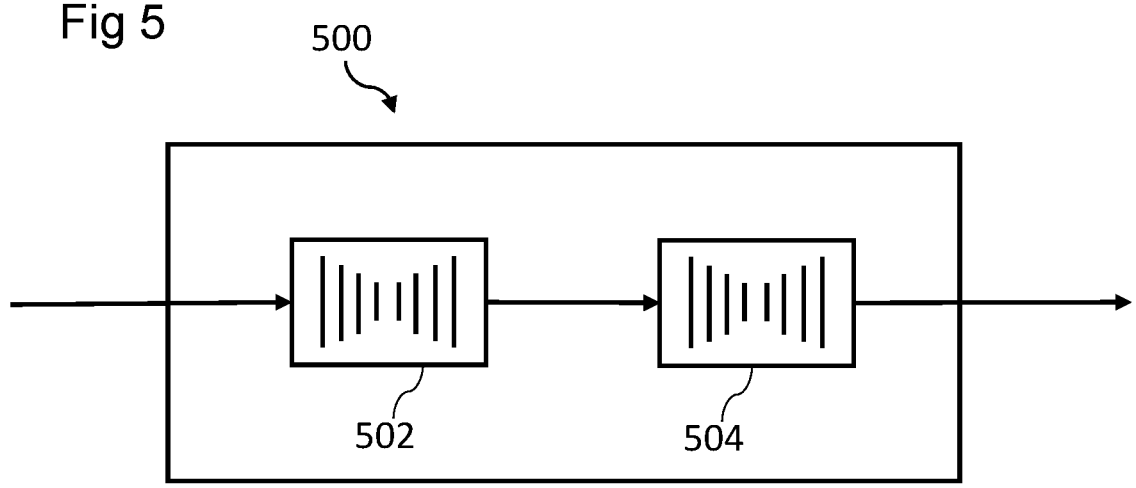
Figure 6A:
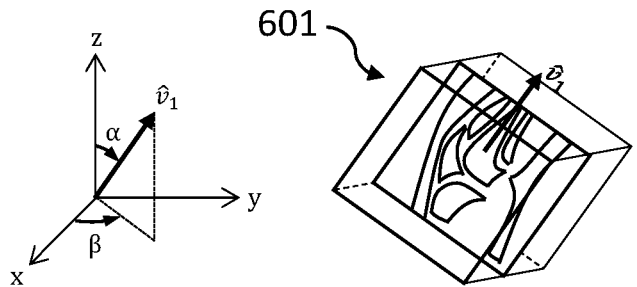
Figure 6B:
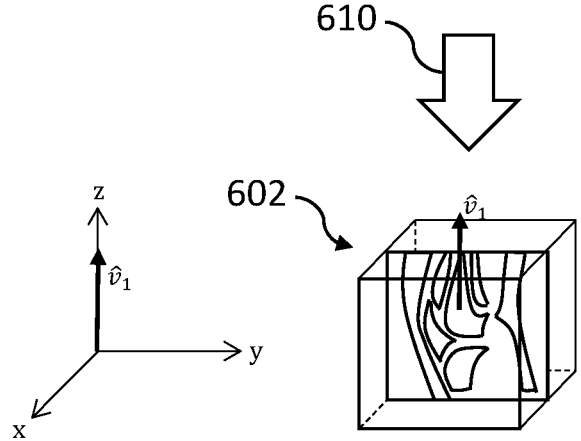
Figure 6C:
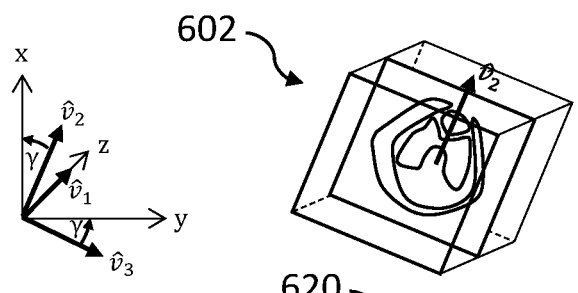
Figure 6D:
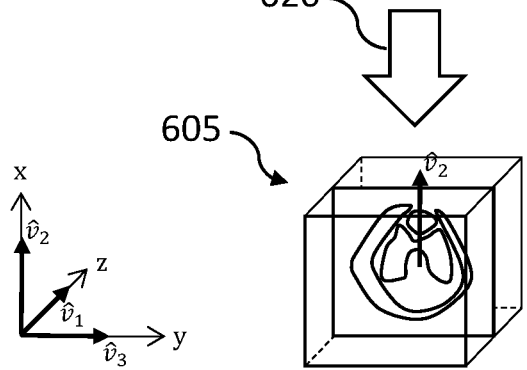
Figure 7:
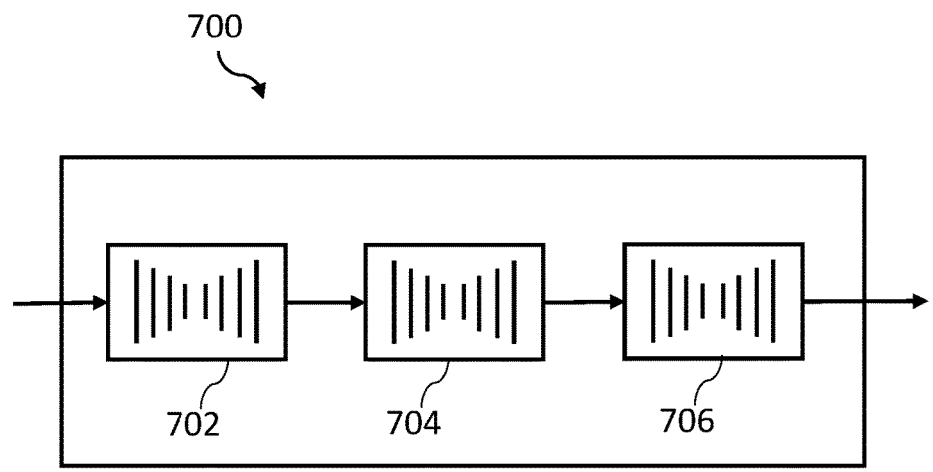
Figure 9:
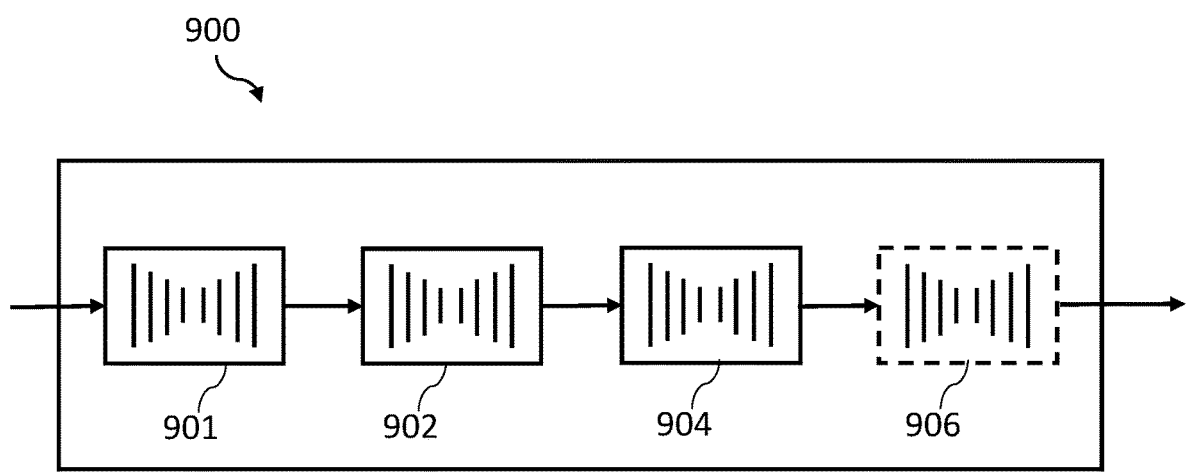
Figure 8:
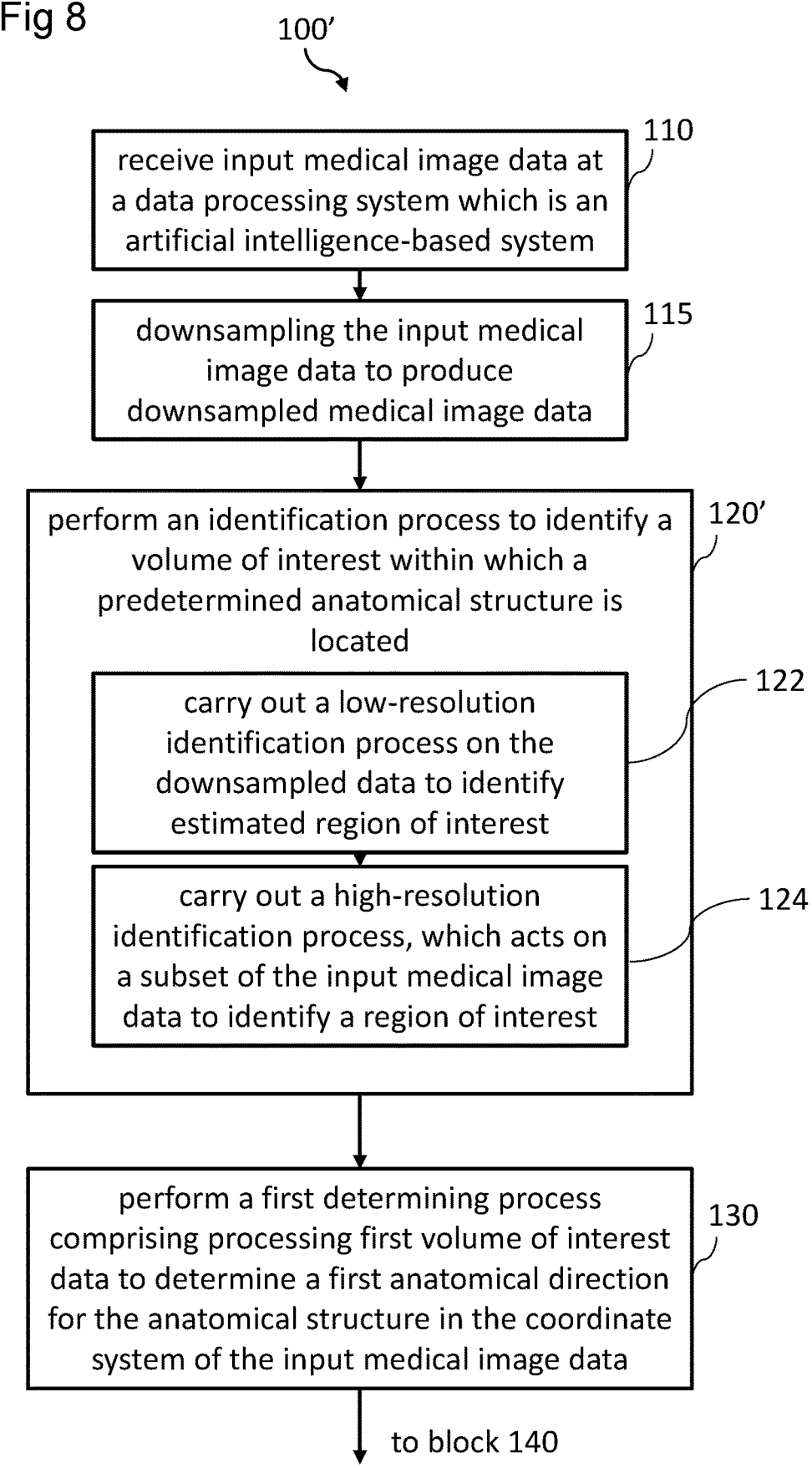
Figure 10:
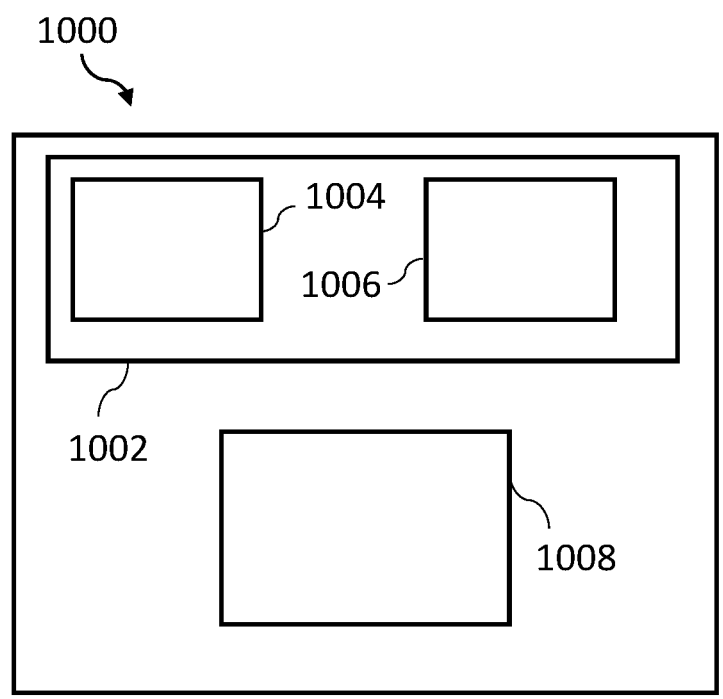

Intentionally Omitted;

FIG. 5 is a schematic diagram illustrating a data processing system, at which the processes described with reference to FIGS. 1-4 may be performed; and FIGS. 6A-6D illustrates further examples of the method of FIG. 1;

FIG. 7 is a schematic diagram illustrating a data processing system, at which the processes described with reference to FIGS. 6A-6D may be performed; and FIG. 8 is a flow diagram illustrating a method for processing medical image data, according to a further example;

FIG. 9 is a schematic diagram illustrating a data processing system, at which the processes described with reference to FIG. 8 may be performed; and FIG. 10 is a schematic diagram illustrating a computing apparatus, according to an example;

DETAILED DESCRIPTION

Figure 1:
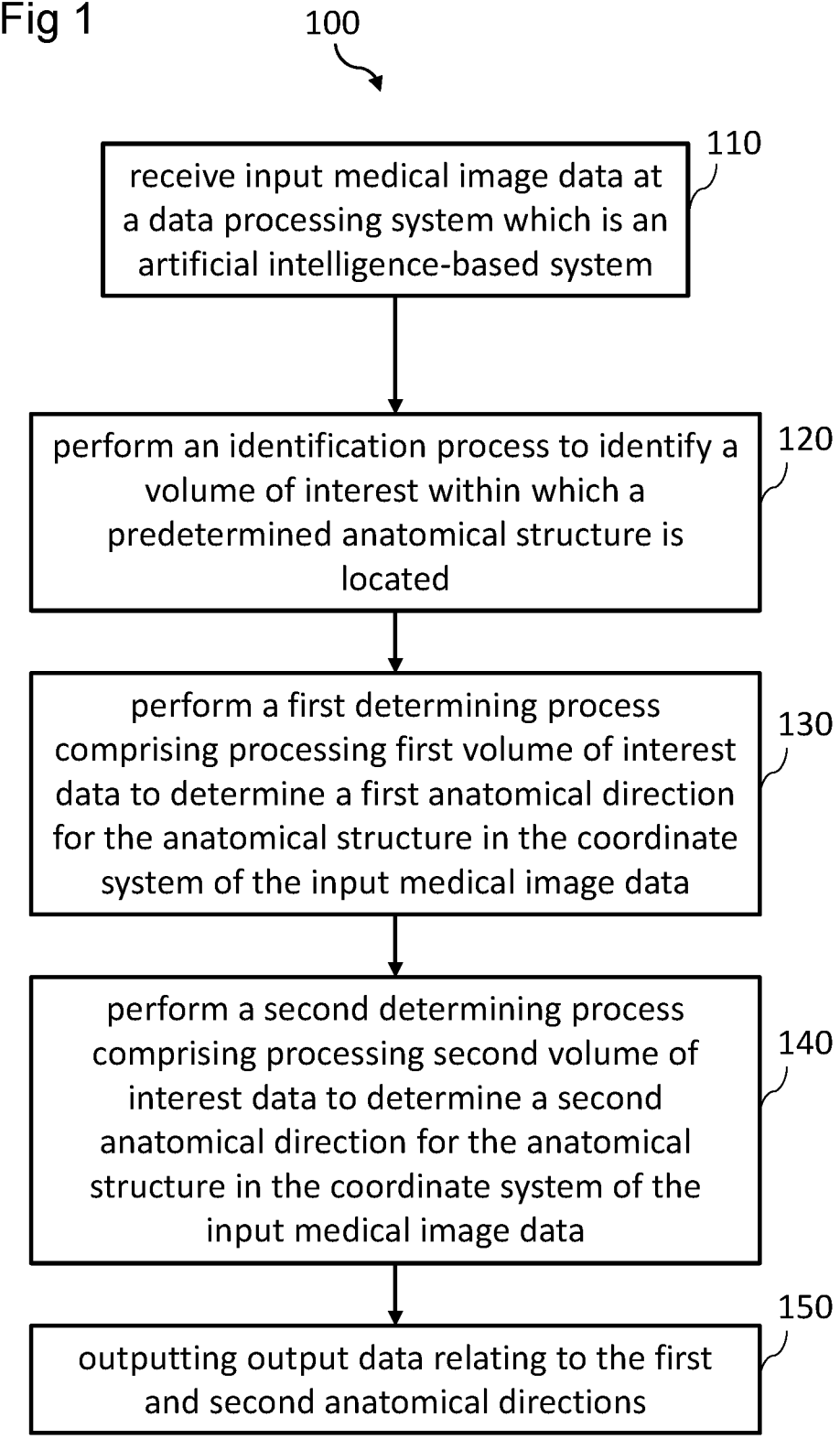
FIG. 1 is a flow diagram illustrating a method for processing medical image data, according to an example.

FIG. 1 is a block diagram illustrating a method 100 for processing medical image data. The method 100 is hereafter referred to as the medical image processing method 100.

At block 110 of the medical image processing method 100, input medical image data is received at a data processing system. The data processing system may be an artificial intelligence-based system, such as a machine learning-based system. Examples and further details regarding the data processing systems are provided further below. The medical image data may be MRI image data, X-ray image data, computed tomography scan data, ultrasound data, or any other kind of medical image data.

The input medical image data 200 may represent an image volume within the human or animal body. Thus, the input medical input data may be said to be three-dimensional data, being defined with reference to a data coordinate system. In some examples, the data coordinate systems may have three axial directions, which may be mutually orthogonal axial directions; for example, they may be x, y and z axis directions. However, in other examples, the axial directions might more generally be in a known angular relationship with each other. Still more generally, the data coordinate system may use spherical or cylindrical coordinates, or some other 3D coordinate system.

The medical image data may have been acquired using a three-dimensional (3D) acquisition process, so that it is inherently in a 3D format. Accordingly, the image data may, for example, be made up of a number of voxels. As an alternative, the input medical input data may have been derived from a set of two dimensional (2D) images in one or more imaging planes, with each of the 2D images being made up of a number of pixels.

Figure 2:
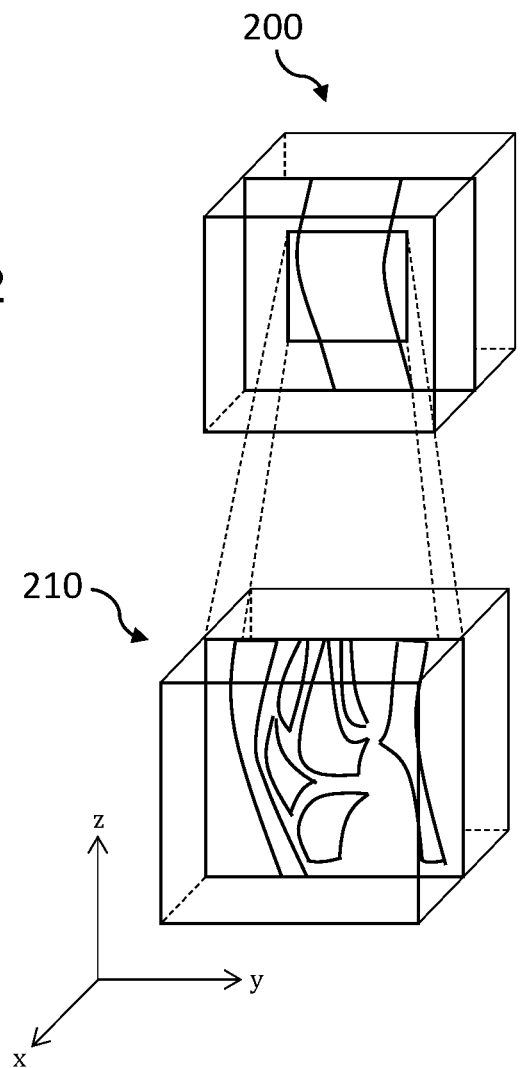
FIG. 2 is a schematic diagram representing processes for identifying a volume of interest that may be performed as part of the method illustrated in FIG. 1.

At block 120, an identification process is performed, at the data processing system, on the input medical image data 200 to identify a volume of interest, within which a predetermined anatomical structure is located. An example of the identification of a volume of interest 210 is illustrated in FIG. 2. FIG. 2 also illustrates the larger volume that is represented by the input medical image data 200. In the example shown, the anatomical structure is a knee joint; however, the principles disclosed herein may be applied to various anatomical structures. For instance, the anatomical structure could instead be a shoulder joint, a hip joint, or the spine.

In the following examples, the volume of interest 210 is a region of the image volume represented by the input image data 200 where the predetermined anatomical structure is located.

At block 130 of the medical image processing method 100, a first determination process is performed at the data processing system. The first determination process comprises processing first volume of interest data to determine a first anatomical direction for the anatomical structure.

An anatomical direction is a direction that is defined by anatomical features, for example in accordance with established medical convention. Hence, an anatomical direction might also be referred to as a canonical direction.

As an example, an anatomical direction could be a direction normal to the sagittal plane, the coronal plane or the transverse plane of a patient. It should therefore be understood that an anatomical direction may, for example, be defined by landmarks within or adjacent the anatomical structure of interest.

In many cases, the anatomical directions will be defined in such a way that they are in a predetermined angular relationship. For instance, they may be mutually orthogonal.

In general, where an anatomical structure is imaged, its precise anatomical directions in the data coordinate system will not be known. This may be the case even where efforts are made to hold a body part being imaged in a desired position and orientation relative to the imaging apparatus, for example using restraints or supports. Thus, there will typically be some unknown angular offset between the anatomical directions of an anatomical structure and the axial directions of the data coordinate system. As mentioned above, such a lack of alignment may complicate later analysis of the medical image data, whether by a medical professional or by a data processing system.

Returning to FIG. 1, in block 130, the first anatomical direction, as defined within the data coordinate system, is determined. Hence, the angular offset between the first anatomical direction and the orthogonal axial directions of the data coordinate system may be implicitly or explicitly determined.

As mentioned above, the first determination acts on first volume of interest data. In general, the first volume of interest data is representative of the volume of interest 210 that is identified in block 120, and is derived from the input medical image data 200 that is received in block 110. Indeed, in some examples, the first volume of interest data may simply be the subset of the input medical image data that corresponds to the volume of interest. In such cases, the medical image processing method 100 may additionally comprise a step of cropping the input medical image data 200 to the subset of image data corresponding to the volume of interest 210, so as to yield the first volume of interest data.

In other examples, the first volume of interest data might be derived by performing further processes on the subset of the input medical image data that corresponds to the volume of interest, such as an enhancement process. Methods according to such examples may include a cropping step prior to or after the performance of such additional processes.

At block 140 of the medical image processing method 100, a second determination process is performed at the data processing system. The second determination process comprises processing second volume of interest data to determine a second anatomical direction for the anatomical structure. Similarly to block 130, in block 140 the second anatomical direction is determined in the data coordinate system and, hence, the angular offset between the second anatomical direction and the axial directions of the data coordinate system may be implicitly or explicitly determined.

In general, the second volume of interest data is representative of the volume of interest that is identified in block 120, and is derived from the input medical image data that is received in block 110.

In some examples, the second volume of interest data may simply be the subset of the input medical image data that corresponds to the volume of interest. In such cases, the medical image processing method 100 may comprise a step of cropping the input medical image data 200 to the subset of image data corresponding to the volume of interest 210, so as to yield the second volume of interest data. It should further be appreciated that the first volume of interest data may be the same as (or substantially the same as) the second volume of interest data.

In other examples, the second volume of interest data might be derived by performing further processes on the subset of the input medical image data that corresponds to the volume of interest, such as an enhancement process. Methods according to such examples may include a cropping step prior to or after the performance of such additional processes.

In still other examples, such as the example described below with reference to FIGS. 6A-6D, the second volume of interest data may be derived from the first volume of interest data. For example, as described with reference to FIGS. 6A-6D, a rotation process may be applied to the first volume of interest data so as to yield the second volume of interest data. This may be considered an example of the second volume of interest data being derived, at least implicitly, using the result of the first determination process.

Returning to FIG. 1, at block 150 of the medical image processing method 100, output data, which relates to the first and second anatomical directions (as determined in blocks 130 and 140), is output by the data processing system.

In some examples, the output data may comprise processed volume of interest data 310', which has been produced by applying a rotation operation to the first volume of interest data and/or the second volume of interest data.

Figure 3A:
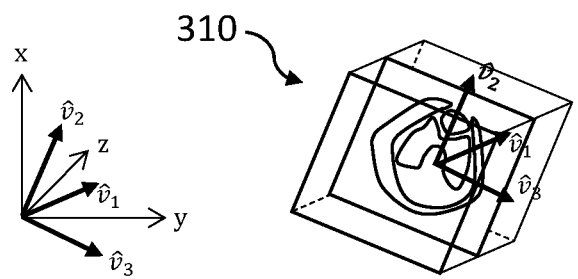
FIGS. 3A-3B illustrate the effect of applying a rotation operation to data representing a volume of interest.
Figure 3B:
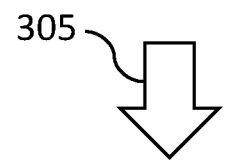
Figure 3B:
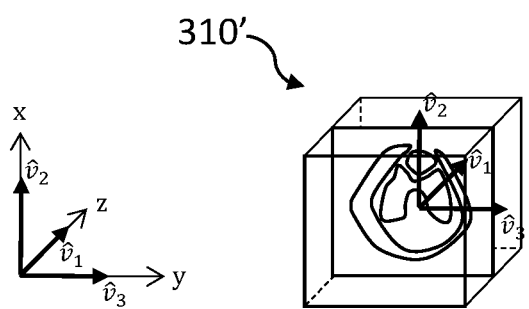

Such an example is illustrated in FIGS. 3A-3B, in which FIG. 3A depicts volume of interest data 310 prior to the rotation operation (which, as noted, may be first volume of interest data and/or second volume of interest data), and FIG. 3B depicts the processed volume of interest data 310'.

As a result of the rotation operation (indicated by arrow 305), the first and second anatomical directions $v_1$, $v_2$, are in a predetermined angular relationship with the axial directions of the data coordinate system for the processed volume of interest data 310'. In the particular example shown, the predetermined angular relationship corresponds to each anatomical direction, $v_1$, $v_2$, being aligned with a respective one of the axes of the data coordinate system. Thus, as shown, first anatomical direction $v_1$ is aligned with the z-axis of the data coordinate system, second anatomical direction $v_2$ is aligned with the x-axis and third anatomical direction $v_3$ is aligned with the y-axis.

Because the anatomical directions of such processed volume of interest data 310' are in a predetermined angular relationship with the axial directions of the data coordinate system, the processed volume of interest data 310' may provide a consistent representation of the anatomical structure. This may, for example, assist in later analysis of the data, whether carried out by a medical professional (who may find a consistent representation of the specific anatomy more intelligible) or by a data processing system, such as an artificial intelligence-based system (which may give less accurate results where the anatomical structure, as represented within the image data, is not in a standardized orientation).

While in the example illustrated in FIGS. 3A-3B the output data comprise processed volume of interest data 310', in other examples, the output data might simply comprise data representing, or defining, the first and second anatomical directions, $v_1$ and $v_2$, in the data coordinate system.

Such output data may, for example, enable a different data processing system to generate representations of the input medical image data 200 in which the anatomical structure has been rotated to be aligned with the anatomical directions.

Alternatively, such output data might be used to indicate to a user (who may be a medical professional) the anatomical directions of a structure being imaged. For example, a user interface might be provided that uses arrows, or other graphical indicators, to indicate to the user the anatomical directions of a structure being imaged. For example, the interface might show the user an image of the anatomy being imaged, with the graphical indicators displayed alongside or over the anatomy.

Indicating to a user the anatomical directions of a structure being imaged may, for example, enable the user to re-orient the body part being imaged so that it is in a desired orientation, such as an orientation that assists with the imaging of the body part. For instance, consider a case where an imaging system has a different in-plane imaging resolution (as is the case with MR imaging, for example); in such a case, the user can re-orient the body part being imaged so that important details of the structure can benefit from the higher resolution. Indeed, in some embodiments, the anatomical directions may be indicated to the user in real time, during a scan, so that he/she may adjust the patient's position relative to the imaging apparatus in real time.

As a further option, the output data may comprise data defining the volume of interest 210. For example, the output data may define the centre of the volume of interest and/or may define the boundary of the volume of interest. Such data may assist a medical profession in carrying out further scans on the volume of interest in order to capture important details of the anatomical structure, for example by carrying out such further scans at a higher level of resolution.

As noted above, in many cases, the anatomical directions may be defined in such a way that they are in a predetermined angular relationship with one another. For instance, the anatomical directions may be mutually orthogonal. As a result, where first and second anatomical directions, $v_1$, $v_2$, are known, a third anatomical direction, $v_3$, may also be implicitly known. Thus, the output data, which relates to the first and second anatomical directions, may provide sufficient information that the third anatomical direction can be determined by a simple calculation using the first and second anatomical directions.

Further examples of processes described above in relation to the medical image processing method 100 are hereafter described with reference to FIG. 4. FIG. 4 illustrates an example of the first and second determination processes described above in relation to blocks 130 and 140. In this example, input medical image data 200 is received that is representative of a patient's leg. A volume of interest 210 is identified within which the knee joint is located.

In the illustrated example, the medical image processing method 100 comprises first and second segmentation processes, which respectively determine first and second planar masks 401, 402, as depicted in FIG. 4. As may be apparent from FIG. 4, the first and second planar masks 401, 402 are orthogonal to one another. In the method illustrated in FIG. 4, these planar masks 401, 402 are used to determine anatomical directions $v_1$, $v_2$ for the anatomical structure. Specifically, normal directions for the planar masks 401, 402 are designated as the first and second anatomical directions $v_1$, and $v_2$.

In specific examples, principal component analysis may be used to determine the normal directions for the first and second planar masks 401, 402 from the planar masks 401, 402. Such an approach may in particular be employed where the planar masks are not precisely two-dimensional, having some thickness, so they are not planes in the strict geometric sense, but rather substantially flat masks, each having a thickness dimension that is a small fraction of the thickness and height dimensions.

The segmentation of the volume of interest data may be performed using an AI-based system configured to perform segmentation of images. In some examples, a machine learning-based system may be used. For example, a deep learning-based (DL-based) segmentation process may be used which uses a neural network such as a convolutional neural network (CNN) employing an encoding and decoding mechanism which has an encoding stage and a decoding stage. In such examples, in the encoding stage, a given input image is projected into non-linear sub-spaces. At earlier layers in the encoding stage, projecting the input image in this way may lead to the identification of simple features (e.g. edges, corners, etc.). In later layers in the encoding stage, more complex features may be identified (e.g. particular shapes, etc.).

FIG. 5 illustrates an example of a data processing system 500 at which the processes described with reference to FIGS. 1-4 may be performed. As described above, the data processing system 500 is an AI-based system. The data processing system 500 may comprise one or more AI-based sub-systems for performing the above described processes.

As shown, the example AI-based system 500 of FIG. 5 comprises a first AI-based sub-system, in the form of a first neural network 502, and a second AI-based sub-system in the form of a second neural network 504.

In the example shown, the first neural network 502 has been trained so that it can perform the identification processes described above with reference to FIGS. 1-4.

More particularly, the first neural network 502 may be trained using a set of training data comprising a set of ground truth image datasets, each of which is representative of a bodily region that includes an instance of the anatomical structure of interest. For instance, where the anatomical structure of interest is the knee joint, each dataset might be representative of the leg, or the lower half of the body. In addition to comprising data representative of such a bodily region, each dataset comprises information relating to a volume of interest within which the instance of the anatomical structure is located. For instance, the information might indicate a bounding box for such a volume of interest, and/or it might indicate a centre for the volume of interest.

During training, the first neural network 502 may, for example, process a given image dataset and compare the generated volume of interest information with the volume of interest information associated with the given ground truth image dataset. A loss function indicating the error between the generated information and the information associated with the set of ground truth image datasets may be reduced by adjusting the weights which control the first neural network 502. The training process may be iterated to reduce or minimize the loss function as required.

The ground truth volume of interest information described above may, for example, be prepared based on examination of the images in question by medical professionals. For instance, a medical professional might examine the images and provide labels or indications, as appropriate. In one example, the medical professional might indicate a volume of interest explicitly, e.g. by indicating a bounding box for the volume of interest and/or by indicating a centre for the volume of interest. Alternatively, the medical professional might indicate a volume of interest implicitly, for instance by indicating the locations of various landmarks, with the volume of interest being calculated based on the locations of these landmarks according to an algorithm.

The example second neural network 504 shown in FIG. 5 is trained so that it can perform both the first and second determination processes described above with reference to FIG. 4.

Accordingly, the second neural network 504 may be trained using a set of training data that comprises a set of ground truth image datasets, each of which is representative of an instance of the anatomical structure. In addition, each dataset comprises information relating to first and second anatomical directions for the instance of the predetermined anatomical structure.

During training, the second neural network 504 may, for example, process a given image dataset to generate first and second planar masks; first and second anatomical directions may in turn be generated from these masks. These generated first and second anatomical directions may then be compared with the anatomical directions indicated in the information associated with the given ground truth image dataset. A loss function indicating the error between the generated output and the directions associated with the set of ground truth image datasets may be reduced by adjusting the weights which control the first neural network 502. The training process may be iterated to reduce or minimize the loss function as required.

The ground truth direction information may, for example, be prepared based on examination of the associated image datasets by medical professionals. For instance, a medical professional might examine the images and provide labels or indications, as appropriate. In one example, the medical professional might indicate a first anatomical direction implicitly, for instance by indicating the locations of various landmarks, with the direction being calculated based on the locations of these landmarks according to an algorithm. Alternatively, the medical professional might indicate a first anatomical direction explicitly, e.g. using a user interface that projects the direction onto an image showing the anatomical structure, and that allows the medical professional to modify the direction as desired.

Particularly (but not exclusively) where the ground truth masks are prepared based on examination of the associated image datasets by medical professionals, the planar masks determined by the trained neural networks may be representative not only of humanly recognizable features of the anatomical structure, but also of abstract context, which a medical professional might not be able to discern.

Various structures may be suitable for the first and second neural networks 502, 504. In a number of examples, the first and second neural networks 502, 504 may be three-dimensional networks. However, in certain examples, they may be two-dimensional networks.

With regard to the first neural network 502, this may, for example, be a region-based convolutional neural network (e.g. 3D versions of rCNN, fast rCNN, or faster rCNN).

Such neural networks are considered particularly suitable for determining volumes of interest using typical medical image datasets.

With regard to the second neural network 504, this may, for example, be a fully convolutional network (FCN) and, in particular examples, a U-net or a V-net. Such neural networks are considered particularly suitable for determining planar masks using typical medical image datasets.

In addition, it should be noted that, while in the specific examples shown in FIG. 5 a single neural network (second neural network 504) performs both the first and second determination processes, it is envisaged that, in other examples, respective neural networks (for example operating in parallel) could perform these processes.

FIGS. 6A-6D illustrate further examples of the medical image processing method 100 of FIG. 1. In the illustrated example, the first and second determination processes of blocks 130 and 140 are carried out in series, with the first anatomical direction $v_1$ being implicitly used in the second determination process.

Attention is first directed to FIG. 6A, which illustrates first volume of interest data 601. As shown, a first anatomical direction, $v_1$, has been determined for the anatomical structure by carrying out the first determination process of block 130.

The example medical image processing method 100 illustrated in FIGS. 6A-6D, comprises, in addition to the processes shown in FIG. 1, applying a first rotation operation to the first volume of interest data, as indicated by arrow 610. As shown in FIG. 6B, the first rotation operation 610 yields the second volume of interest data 602, which is used in the second determination process of block 140. As is apparent from a comparison of FIGS. 6A and 6B, this rotation results in the first anatomical $v_1$ direction becoming aligned with an axis of the data coordinate system. (In the example shown, the z-axis.) This rotation may assist the operation of the second determination process, as the second volume of interest data may be more "recognizable" since it is closer to a standardized orientation.

Attention is next directed to FIG. 6C, which illustrates second volume of interest data 602. As shown, a second anatomical direction, $v_2$ (which is orthogonal to the first anatomical direction, $v_1$) has been determined for the anatomical structure by carrying out the second determination process of block 140.

As noted above, the first anatomical direction, $v_1$, may be used in the second determination process of block 140. In particular, the second determination process may, in some examples, be constrained such that it determines a second anatomical direction, $v_2$, that is orthogonal to the first anatomical direction, $v_1$, as already determined by the first determination process. In such examples, the second determination process might be described as determining a rotation angle (indicated as γ in FIG. 6C), which aligns the second direction, $v_2$, with one of the axes of the data coordinate system (in the example shown in FIG. 6C, the x axis). However, in other examples, such a constraint is not imposed on the second determination process.

Returning to FIG. 6C, as indicated by arrow 620, the method of FIGS. 6A-6D comprises applying a second rotation operation to the second volume of interest data 602, yielding processed volume of interest data 605. This rotation operation aligns the other two anatomical directions, $v_2$ and $v_3$, with the other two axial directions of the data coordinate system. The processed volume of interest data 605 may then be included within the output data that is output from the data processing system in block 150. Because such processed volume of interest data 605 is defined with reference to anatomical directions, it may provide a consistent representation of the anatomical structure. This may, for example, assist in later analysis of the data, whether carried out by a medical professional (who may find a consistent representation of the specific anatomy more intelligible) or by a data processing system, such as an artificial intelligence-based system (which may give less accurate results where the anatomical structure, as represented within the image data, is not in a standardized orientation).

FIG. 7 illustrates an example of a data processing system 700 at which the processes described with reference to FIGS. 6A-6D may be performed. As described above, the data processing system is an AI-based system. The data processing system may comprise one or more AI-based sub-systems for performing the above described processes.

FIG. 7 illustrates an example AI-based system 700 comprising a first AI-based sub-system, in the form of a first neural network 702, and second and third AI-based sub-systems in the form of a second and third neural networks 704, 706.

In the example shown, the first neural network 702 has been trained so that it can perform the identification processes described above with reference to FIGS. 1-2.

More particularly, the first neural network 702 may be trained using a set of training data comprising a set of ground truth image datasets, each of which is representative of a bodily region that includes an instance of the anatomical structure of interest. For instance, where the anatomical structure of interest is the knee joint, each dataset might be representative of the leg, or the lower half of the body. In addition to comprising data representative of such a bodily region, each dataset comprises information relating to a volume of interest within which the instance of the anatomical structure is located. For instance, the information might indicate a bounding box for such a volume of interest, and/or it might indicate a centre for the volume of interest.

As may be appreciated, the first neural network can be trained according to one of the approaches described above with reference to the first neural network 502 of FIG. 5.

The second neural network 704 shown in FIG. 7 is trained so that it can perform the first determination process described above with reference to FIGS. 1 and 6A-6D.

Accordingly, the second neural network 704 may be trained using a set of training data that comprises a set of ground truth image datasets, each of which is representative of an instance of the anatomical structure. In addition, each dataset comprises information relating to a first anatomical direction for the instance of the anatomical structure represented within the dataset.

During training, the second neural network 704 may, for example, process a given image dataset and compare the generated first anatomical direction with the first anatomical direction indicated in the information associated with the given ground truth image dataset. A loss function indicating the error between the generated direction and the direction associated with the set of ground truth image datasets may be reduced by adjusting the weights which control the second neural network 704. The training process may be iterated to reduce or minimize the loss function as required.

The ground truth masks may, for example, be prepared based on examination of the associated image datasets by medical professionals. For instance, a medical professional might examine the images and provide labels or indications, as appropriate. In one example, the medical professional might indicate a first anatomical direction implicitly, for instance by indicating the locations of various landmarks, with the direction being calculated based on the locations of these landmarks according to an algorithm. Alternatively, the medical professional might indicate a first anatomical direction explicitly, e.g. using a user interface that projects the direction onto an image showing the anatomical structure, and that allows the medical professional to modify the direction as desired.

The third neural network 706 shown in FIG. 7 is trained so that it can perform the second determination process described above with reference to FIGS. 1 and 6A-6D.

Accordingly, the third neural network 706 may be trained using a set of training data that comprises a set of ground truth image datasets, each of which is representative of an instance of the anatomical structure. In addition, each dataset comprises information relating to a second anatomical direction for the instance of the anatomical structure represented within the dataset.

During training, the third neural network 706 may, for example, process a given image dataset and compare the generated second anatomical direction with the second anatomical direction indicated in the information associated with the given ground truth image dataset. A loss function indicating the error between the generated direction and the direction associated with the set of ground truth image datasets may be reduced by adjusting the weights which control the third neural network 706. The training process may be iterated to reduce or minimize the loss function as required.

The ground truth masks may, for example, be prepared based on examination of the associated image datasets by medical professionals. For instance, a medical professional might examine the images and provide labels or indications, as appropriate. In one example, the medical professional might indicate a second anatomical direction implicitly, for instance by indicating the locations of various landmarks, with the direction being calculated based on the locations of these landmarks according to an algorithm. Alternatively, the medical professional might indicate a second anatomical direction explicitly, e.g. using a user interface that projects the direction onto an image showing the anatomical structure, and that allows the medical professional to modify the direction as desired.

Various structures may be suitable for the first, second and third neural networks 702, 704, 706. In specific examples, the second and third neural networks 704, 706 may be capsule networks. Such neural networks are considered particularly suitable for determining anatomical directions using typical medical image datasets. The first neural network 702 might also be a capsule network, or might be region-based convolutional neural network (e.g. rCNN, fast rCNN, or faster rCNN), as with the first neural network 502 shown in FIG. 5.

Attention is now directed to FIG. 8, which illustrates a modified version 100' of the medical image processing method 100 shown in FIG. 1. The method 100' of FIG. 8 is generally the same as the medical image processing method 100 shown in FIG. 1, except in that the identification process 120' in the method of FIG. 8 comprises two (sub)processes: a low-resolution identification process 122 and a high-resolution identification process 124, and in that the method 100' comprises an additional, associated step of downsampling the input medical image data, illustrated in block 115.

As shown in FIG. 8, the step of downsampling the input medical image data illustrated in block 115 produces downsampled medical image data. The low-resolution identification process 122 acts on this downsampled data to identify an estimated volume of interest. The high-resolution identification process 124 can then act on a subset of the input medical image data representing the estimated volume of interest so as to identify the volume of interest that is analysed in blocks 130 and 140. Such an identification process 120' is considered to assist in accurately and robustly identifying a volume of interest, while being efficient in terms of time and/or storage requirements.

As may be appreciated, the method 100' shown in FIG. 8 may incorporate any of the first and second determination processes and additional processes described above with reference to FIGS. 1-7.

FIG. 9 illustrates an example of a data processing system 900 at which the processes described with reference to FIG. 8 may be performed. As described above, the data processing system 900 is an AI-based system. The data processing system 900 may comprise one or more AI-based subsystems for performing the above described processes.

As shown, the example AI-based system 900 of FIG. 9 comprises a first AI-based sub-system, in the form of a first neural network 901, a second AI-based sub-system in the form of a second neural network 902, a third AI-based sub-system in the form of a third neural network 904, and, optionally, a fourth AI-based sub-system in the form of a fourth neural network 906.

In the example shown, the first and second neural networks 901, 902 have been trained so that they can perform, respectively, the low-resolution identification process 122 and the high resolution identification process 124 described above with reference to FIG. 8. As may be appreciated, each of the first and second neural networks 901, 902 can be trained according to one of the approaches described above with reference to the first neural network 502 of FIG. 5.

The training of first neural network 901 might differ from that of second neural network 902 in that the ground truth image datasets used for first neural network 901 may be of lower resolution than those used for second neural network 902; for instance, the training data for second neural network 902 could be downsampled and then used for first neural network 901.

As may be appreciated, various structures may be suitable for the first and second neural networks 901, 902. For example, one or both of these neural networks may be a region-based convolutional neural network (e.g. rCNN, fast rCNN, or faster rCNN).

It should further be noted that first and second neural networks may have generally the same structure as each other. Indeed, in some examples, the first and second neural networks may differ substantially only in that a feature size of the first (low-resolution) network 901 is different to (e.g. larger than) a feature size of the second (high-resolution) network 902.

In some examples, third neural network 904 may be configured and trained in generally the same manner as second neural network 504 of FIG. 5. In other examples, in particular where the example AI-based system 900 includes fourth neural network 906, the third and fourth neural networks 904, 906 may be configured and trained in generally the same manner as, respectively, second and third neural networks 704 706 of FIG. 7.

Attention is now directed to FIG. 10, which schematically illustrates an apparatus 1000 for processing medical image data. The apparatus 1000 comprises a computing device in the form of a computer 1002. The computer 1002 comprises one or more processors 1004 and a memory 1006. The memory 1006 may be in the form of a computer readable storage medium. The memory 1006 has stored on it one or more neural networks trained to determine one or more characteristics relating to one or more abnormalities relating to one or more target tendons in medical image data. For example, the memory 1006 may have the neural networks described above stored on it. The memory 1006 may also store instructions that when executed by the one or more processors 1004, cause the one or more processors to perform the medical image processing method described above. The one or more processors may comprise one or more Graphics Processing Units (GPUs), for example, or other types of processors. The use of GPUs may optimize the apparatus 1000 for making use of the described neural networks. This is because, as will be appreciated, a GPU can handle a large number of threads at the same time.

The one or more neural networks and the instructions may be stored on the memory 1006 when the apparatus 1000 is supplied to a user. Alternatively, the one or more neural networks and the instructions may be supplied thereafter (e.g. in the form of a computer program product) by means of a computer readable storage medium such as a compact disk (CD), a digital versatile disk (DVD), hard disk drive, solid state drive, a flash memory device and the like. Alternatively, the one or more neural networks and the instructions may be downloaded onto the storage medium 1006 via a data communication network (e.g. the world-wide web).

In some examples, the apparatus 1000 may also comprise an imaging apparatus 1008 configured to acquire the medical image data. For example, the apparatus 1000 may include an MRI image acquisition machine as well as the computer 1002.

In some examples, the apparatus 1000 may comprise an input interface such as a mouse, a keyboard (or respective connection interfaces for connecting same), a touch screen interface and the like. A user of the apparatus 1000 may use the input interface to input information into the apparatus 1000. For example, the user may manually correct and/or override the output of the apparatus 1000. For instance, if the apparatus 1000 provides first and second anatomical directions for an anatomical structure, based on input medical image data, and the user (a medical professional) judges that these directions are incorrect or inaccurate, he/she may indicate first and/or second anatomical directions. Similarly, if a user judges that the volume of interest, as determined by the apparatus 1000 is incorrect or inaccurate, he/she may indicate a corrected volume of interest for the anatomical structure.

While the invention has been illustrated and described in detail in the context of specific examples, the invention is not limited to the disclosed examples. Other variations can be deducted by those skilled in the art without leaving the scope of protection of the claimed invention.

In summary, disclosed is a method, a computer readable storage medium and an apparatus for processing medical image data. Input medical image data is received at a data processing system, which is an artificial intelligence-based system. An identification process is performed at the data processing system on the input medical image data to identify a volume of interest within which an instance of a predetermined anatomical structure is located. First and second determination processes are performed at the data processing system to determine, respectively, first and second anatomical directions for the instance of the anatomical structure that are defined relative to the coordinate system of the input medical image data. Output data relating to the first and second anatomical directions is output from the data processing system.

The invention claimed is:

1. A method for processing medical image data, the method comprising:
  receiving input medical image data at a data processing system, the data processing system being an artificial intelligence-based system, the input medical image data being defined with reference to a data coordinate system;
  performing, at the data processing system, an identification process on the input medical image data to identify a volume of interest within which an instance of a predetermined anatomical structure is located;
  performing, at the data processing system, a first determination process comprising segmenting a first volume of interest data to determine a first planar mask and determining from the first planar mask a first anatomical direction ($v_1$) for the instance of the predetermined anatomical structure, the first volume of interest data being medical image data that is representative of the volume of interest and that is derived from the input medical image data;
  performing, at the data processing system, a second determination process comprising segmenting a second volume of interest data to determine a second planar mask and determining from the second planar mask a second anatomical direction ($v_2$) for the instance of the predetermined anatomical structure, the second volume of interest data being medical image data that is representative of the volume of interest and that is derived from the input medical image data, the first and second anatomical directions ($v_1$, $v_2$) being defined with reference to the data coordinate system; and
  outputting, from the data processing system, output data relating to the first and second anatomical directions ($v_1$, $v_2$).

2. The method according to claim 1, wherein the output data comprise data defining the volume of interest.

3. The method according to claim 1,
  wherein determining from the first planar mask the first anatomical direction ($v_1$) for the instance of the predetermined anatomical structure comprises determining a direction normal to the first planar mask, and designating the normal direction for the first planar mask as the first anatomical direction ($v_1$);
  and wherein determining from the second planar mask the second anatomical direction ($v_2$) for the instance of the predetermined anatomical structure comprises determining a direction normal to the second planar mask, and designating the normal direction for the second planar mask as the second anatomical direction ($v_2$).

4. The method according to claim 3, comprising determining the normal directions for the first and second planar masks using principal component analysis.

5. The method according to claim 3, further comprising applying a rotation operation to at least one of the first volume of interest data and the second volume of interest data, yielding processed volume of interest data, wherein the data coordinate system has three axial directions (x, y, z), wherein the rotation operation results in the first and second anatomical directions ($v_1$, $v_2$) being in a predetermined angular relationship with the axial directions (x, y, z) of the data coordinate system, and wherein the output data comprise the processed volume of interest data.

6. The method according to claim 3, wherein: the data processing system is a neural network system comprising:
  an identification network, which has been trained using training data comprising a set of ground truth image datasets, each of which is representative of a volume encompassing an instance of the predetermined anatomical structure and comprises information relating to a volume of interest within which that instance of the predetermined anatomical structure is located;

one or more determination networks, which have been trained using training data comprising a set of ground truth image datasets, each of which is representative of an instance of the predetermined anatomical structure and comprises information relating to first and second anatomical directions for the instance of the predetermined anatomical structure; and the method comprises: performing the identification process at least in part using the identification network, and performing the first and second determination processes with the one or more determination networks.

7. The method according to claim 1, comprising applying a first rotation operation to the first volume of interest data, yielding the second volume of interest data, wherein the data coordinate system has three axial directions (x, y, z), and wherein the first rotation operation results in the first anatomical direction ($v_1$) being in a predetermined angular relationship with the axial directions (x, y, z) of the data coordinate system.

8. The method according to claim 7, comprising applying a second rotation operation to the second volume of interest data, yielding processed volume of interest data, wherein the second rotation operation results in the first and second anatomical directions ($v_1$, $v_2$) each being in a predetermined angular relationship with the axial directions (x, y, z) of the data coordinate system, and wherein the output data comprise the processed volume of interest data.

9. The method according to claim 1, wherein the second determination process comprises:

receiving, as an input, the first anatomical direction ($v_1$), as determined by the first determination process; and determining the second anatomical direction ($v_2$) based on a constraint that the second anatomical direction is orthogonal to the first anatomical direction.

10. The method according to claim 7, wherein: the data processing system is a neural network system comprising:

an identification network, which has been trained using training data comprising a set of ground truth image datasets, each of which is representative of a bodily region that includes an instance of the predetermined anatomical structure and comprises information relating to a volume of interest within which that instance of the predetermined anatomical structure is located;

a first determination network, which has been trained using training data comprising a set of ground truth image datasets, each of which is representative of an instance of the predetermined anatomical structure and comprises information relating to a first anatomical direction for that instance of the predetermined anatomical structure; and a second determination network, which has been trained using training data comprising a set of ground truth image datasets, each of which is representative of an instance of the predetermined anatomical structure and comprises information relating to a second anatomical direction for that instance of the predetermined anatomical structure;

and the method comprises: performing the identification process at least in part using the identification network, and performing the first and second determination processes with, respectively, the first and second determination networks.

11. The method according to claim 1, comprising downsampling the input medical image data to produce downsampled medical image data, and wherein the identification process comprises:

a low-resolution identification process, which acts on the downsampled medical image data to identify an estimated volume of interest; and a high-resolution identification process, which acts on a subset of the input medical image data representing the estimated volume of interest so as to identify the volume of interest.

12. The method according to claim 11, wherein: the data processing system is a neural network system comprising:

a low-resolution identification network, which has been trained using training data comprising a set of ground truth image datasets, each of which is representative of a bodily region that includes an instance of the predetermined anatomical structure and comprises information relating to a volume of interest within which that instance of the predetermined anatomical structure is located, and a high-resolution identification network which has been trained using training data comprising a set of ground truth image datasets, each of which is representative of a bodily region that includes an instance of the predetermined anatomical structure and comprises information relating to a volume of interest within which that instance of the predetermined anatomical structure is located; and the method further comprises: performing the low-resolution identification process using the low-resolution identification network, and performing the high-resolution identification process using the high-resolution identification network.

13. The method according to claim 1, wherein: the predetermined anatomical structure is a knee joint, a shoulder joint, a hip joint, or a spine.

14. The method according to claim 1, wherein the first and second anatomical directions ($v_1$, $v_2$) are selected from the group consisting of: a direction normal to a sagittal plane; a direction normal to a coronal plane; and a direction normal to a transverse plane.

15. A non-transitory computer readable storage medium, storing:

one or more neural networks trained to identify a volume of interest in which an instance of a predetermined anatomical structure is located, and to determine first and second anatomical directions ($v_1$, $v_2$) for the instance of the predetermined anatomical structure; and instructions that, when executed by a processor, cause the processor to:

receive input medical image data at a data processing system, the data processing system being an artificial intelligence-based system, the input medical image data being defined with reference to a data coordinate system;

perform, at the data processing system, an identification process on the input medical image data to identify a volume of interest within which an instance of a predetermined anatomical structure is located;

perform, at the data processing system, a first determination process comprising segmenting a first volume of interest data to determine a first planar mask and determining from the first planar mask a first anatomical direction for the instance of the predetermined anatomical structure, the first volume of interest data being medical image data that is representative of the volume of interest and that is derived from the input medical image data;

perform, at the data processing system, a second determination process comprising segmenting a second volume of interest data to determine a second planar mask and determining from the second planar mask a second anatomical direction for the instance of the predetermined anatomical structure, the second volume of interest data being medical image data that is representative of the volume of interest and that is derived from the input medical image data, the first and second anatomical directions being defined with reference to the data coordinate system; and output, from the data processing system, output data relating to the first and second anatomical directions.

16. An apparatus for processing medical image data, comprising:

one or more processors; and a memory storing:

one or more neural networks trained to identify a volume of interest in which a predetermined anatomical structure is located, and to determine first and second anatomical directions ($v_1$, $v_2$) for the predetermined anatomical structure, as represented within medical image data; and instructions that, when executed by the one or more processors, cause the one or more processors to:

receive input medical image data at a data processing system, the data processing system being an artificial intelligence-based system, the input medical image data being defined with reference to a data coordinate system;

perform, at the data processing system, an identification process on the input medical image data to identify a volume of interest within which an instance of a predetermined anatomical structure is located;

perform, at the data processing system, a first determination process comprising segmenting a first volume of interest data to determine a first planar mask and determining from the first planar mask a first anatomical direction ($v_1$) for the instance of the predetermined anatomical structure, the first volume of interest data being medical image data that is representative of the volume of interest and that is derived from the input medical image data;

perform, at the data processing system, a second determination process comprising segmenting a second volume of interest data to determine a second planar mask and determining from the second planar mask a second anatomical direction ($v_2$) for the instance of the predetermined anatomical structure, the second volume of interest data being medical image data that is representative of the volume of interest and that is derived from the input medical image data, the first and second anatomical ($v_1$, $v_2$) directions being defined with reference to the data coordinate system; and output, from the data processing system, output data relating to the first and second anatomical directions.

17. The apparatus according to claim 16, comprising an imaging apparatus configured to provide the input medical image data.

18. The apparatus according to claim 17 comprising: an input interface for allowing a user of the apparatus to override and/or manually correct the output of the apparatus.

* * * * *